(12) United States Patent
Johnson

(10) Patent No.: US 10,420,674 B2
(45) Date of Patent: *Sep. 24, 2019

(54) THERMAL EYE POD ASSEMBLY

(71) Applicant: Robert W. Johnson, Pearl river, LA (US)

(72) Inventor: Robert W. Johnson, Pearl river, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/993,730

(22) Filed: May 31, 2018

(65) Prior Publication Data

US 2018/0271697 A1    Sep. 27, 2018

Related U.S. Application Data

(63) Continuation of application No. 15/423,184, filed on Feb. 2, 2017, now Pat. No. 9,999,539.

(51) Int. Cl.
*A61F 7/02* (2006.01)
*A61F 7/00* (2006.01)

(52) U.S. Cl.
CPC .............. *A61F 7/02* (2013.01); *A61F 7/0241* (2013.01); *A61F 2007/0004* (2013.01); *A61F 2007/0225* (2013.01); *A61F 2007/0233* (2013.01); *A61F 2007/0295* (2013.01)

(58) Field of Classification Search
CPC ...... A61F 2007/0004; A61F 2007/0225; A61F 2007/0233; A61F 2007/0295; A61F 7/02; A61F 7/0241

See application file for complete search history.

(56) References Cited

U.S. PATENT DOCUMENTS

| 3,111,166 | A | * | 11/1963 | Munz | F25B 21/02 165/263 |
| 3,768,485 | A | | 10/1973 | Linick | |
| 4,027,727 | A | * | 6/1977 | Pullens | A47J 39/006 165/48.1 |
| 8,784,391 | B1 | | 7/2014 | Biser | |
| 2008/0296286 | A1 | | 12/2008 | Liang | |
| 2009/0287283 | A1 | | 11/2009 | Biser | |
| 2017/0049614 | A1 | * | 2/2017 | Paulson | A61F 7/02 |

* cited by examiner

*Primary Examiner* — Michael F Peffley
(74) *Attorney, Agent, or Firm* — James Creighton Wray

(57) ABSTRACT

A thermal eye pod assembly for use in efficiently heating and/or cooling a plurality of thermal eye patch members, as desired. A portable thermal eye pod assembly for use in efficiently treating a user's recurring ophthalmic conditions, accelerating a user's healing process, and providing a user with a relatively faster means of pain relief.

17 Claims, 4 Drawing Sheets

THERMAL EYE POD ASSEMBLY

This application is a continuation of application Ser. No. 15/423,184 filed Feb. 2, 2017, now U.S. Pat. No. 9,999,539.

STATEMENTS AS TO THE RIGHTS TO THE INVENTION MADE UNDER FEDERALLY SPONSORED RESEARCH AND DEVELOPMENT

NONE

BACKGROUND OF THE INVENTION

Field of the Invention

The present invention pertains to a thermal eye pod assembly for use in heating and/or cooling at least one eye patch. In a heated state, the present invention pertains to a thermal eye pod assembly for use in heating said eye patch in order to treat a variety of different ailments, including, but not limited to chalazions, styes, and dry eye syndrome; in a cooled state, the present invention pertains to a thermal eye pod assembly for use in cooling said eye patch in order to be used to reduce post-operative swelling that is generally associated with a variety of different surgical procedures, blepharoplasty, or any other surgical procedures that are typically performed in a user's orbit area. More particularly, the present invention pertains to a portable thermal eye pod assembly for use in efficiently treating recurring ophthalmic conditions, accelerating the healing process, and for providing a means of faster relief for pain and discomfort to a user.

Brief Description of the Prior Art

Typically, when treating a variety of different eye conditions, a heating process or any other similar means of treatment is necessary. Further, when recovering from a variety of different eye conditions, a cooling process or any other similar means of recovery is generally necessary. Conventionally, when in need of a heating method, a user would place a hot compress, or any other similar heating device, on the affected area, such as, for example, a user's orbital area, but would have to manually hold said hot compress on the area at issue, thus limiting a user in his or her activities at the time of treatment. Further, a hot compress has to be continuously reheated in order to maintain its desired temperature. Moreover, when in need of a cooling method, a user would typically place an ice pack, or any other similar cooling device, on the area at issue; however, while also limiting a user in his or her activities by having to manually hold said ice pack on the affected area, ice packs can leak and can become relatively warm by quickly increasing in temperature, thereby becoming a hassle and an inconvenience to a user.

In addition, these conventional remedies are generally limiting in where a user is able to use them. For example, since these methods require manually holding these remedies on the affected area, a user has to be able to find an appropriate time and place when he or she can stay in a single location without needing the use or his or her hands to be able to do other activities. Additionally, a user would typically need to be near an ice machine and/or a sink when using an ice pack; and, a user would need to be near hot water and/or a heating source when using a hot compress.

As such, there is a need for a device that can heat and/or cool an eye patch to a desired temperature in order to treat eye conditions or assist in the recovery of eye conditions. There is also a need for a heating and/or cooling device that can be securely worn, thereby eliminating a requirement of having to manually hold said treatment devices. Further, there is a need for a device that can portably heat and/or cool said eye patch, thus eliminating any location limitation to a user.

SUMMARY OF THE INVENTION

The present invention pertains to a thermal eye pod assembly generally comprising a frame member, a thermal eye patch member, and an external shell member having a plurality of internal components. In a preferred embodiment, external shell member beneficially comprises a variety of different internal components, including, but not limited to, a power source, a heating source, a circuit board, a fan, and multiple means of insulation. The different internal components of said external shell member are generally installed in a pre-designated position within an inner chamber of said external shell member, thereby creating a method of installation and assembly that is typically easier and more efficient during the manufacturing process. Additionally, said internal components of external shell member cooperate to create a desired temperature within inner chamber of external shell member for use in heating and/or cooling said thermal eye patch member relative to ambient conditions, as necessary.

In a preferred embodiment, the present invention further comprises a transfer plate and a transfer block, wherein said transfer plate and said transfer block allow a desired temperature to be regulated and maintained throughout the internal components of the external shell member. Additionally, said transfer plate is positioned adjacently underneath an eye pod support panel. Said eye pod support panel provides a location for a first and a second eye pod support cup to hold and insulate a plurality of thermal eye patch members, thus allowing said thermal eye patch members to be heated and/or cooled as necessary due to their respective placement near said transfer plate.

In a preferred embodiment, frame member generally comprises a support frame and a first lens and a second lens, wherein first and second lens are attachably connected to support frame. First and second lens each further comprise an aperture for use in providing a means of attachment with said thermal eye patch member. Thermal eye patch member beneficially comprises a plurality of layers with a heat sealed edge, thereby providing a means to maintain a desired temperature within said thermal eye patch. Additionally, thermal eye patch member comprises a support pin that is positioned on an outer layer of thermal eye patch member for use in axially aligning, and thus, attachably connecting to first and/or second lens of frame member. As a result, once thermal eye patch member is heated or cooled relative to ambient conditions as desired, said eye patch member attachably connects to said frame member, thereby allowing a user to wear eye patch member via frame member, as necessary.

BRIEF DESCRIPTION OF THE DRAWINGS/FIGURES

The foregoing summary, as well as any detailed description of the preferred embodiments, is better understood when read in conjunction with the drawings and figures contained herein. For the purpose of illustrating the invention, the drawings and figures show certain preferred embodiments. It is understood, however, that the invention is not limited to the specific methods and devices disclosed in such drawings or figures.

DETAILED DESCRIPTION OF A PREFERRED EMBODIMENT

Figure 1A:
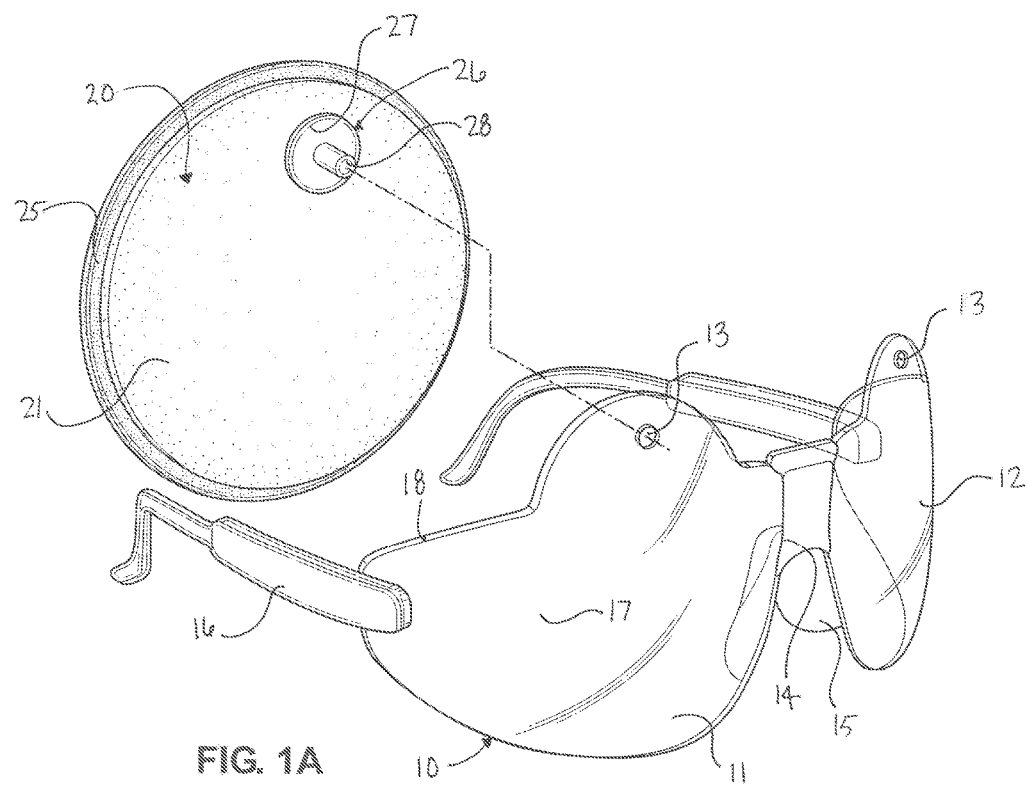
FIG. 1A depicts an exploded perspective view of a preferred embodiment of a thermal eye patch member and a support frame and lens of the present invention.

Referring to the drawings, FIG. 1A depicts an exploded perspective view of a thermal eye patch member 20 and a frame member 10 of the present invention. In a preferred embodiment, thermal eye pod assembly 100 comprises thermal eye patch member 20, wherein said eye patch member 20 has a substantially circular shape and comprises a plurality of different layers. Further, thermal eye patch member 20 comprises a support pin 26 for use in attachably connecting said eye patch member 20 to frame member 10.

Frame member 10 comprises a support frame, a first lens 11, and a second lens 12 in an attachably connected configuration, thus cooperating to form a pair of glasses, or goggles. Support frame attachably connects to first 11 and second lens 12 by way of a nose piece and a plurality of ear frames 16, thereby creating a single, cohesive unit that can be worn by a user. Nose piece comprises a bridge member 14 for use in connecting first 11 and second lens 12 member and a stabilizer 15 for use in providing stability to the present invention when a user is wearing frame member 10. Ear frames 16 extend in a relatively outwardly direction from first 11 and second lens 12 and are used to hook behind a user's ears. First lens 11 and second lens 12 comprise a substantially convex front surface 17 that has a slightly outward curvature from a user's eyes and face when frame member is being worn, and an inner surface 18 that can adjacently adhere to an outer layer 21 of thermal eye patch member 20. In addition, first lens 11 and second lens 12 each further comprise an aperture 13 that can be used to receive a support pin 26 of thermal eye patch member 20. Aperture 13 and support pin 26 provide a means of attachment and connection points for first 11 and second lens 12 to semi-permanently join and attach to thermal eye patch member 20.

Figure 1B:
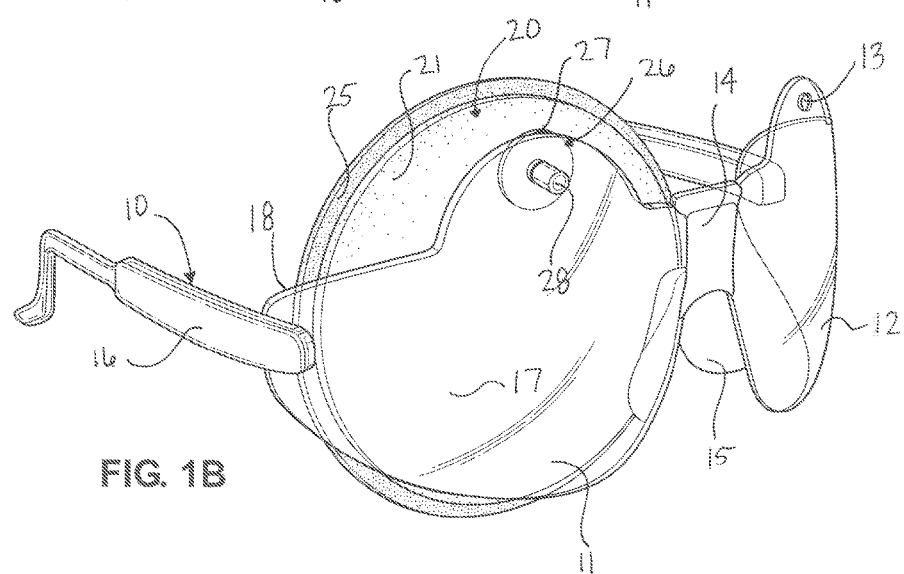
FIG. 1B depicts a perspective view of a preferred embodiment of a thermal eye patch member and a support frame and lens of the present invention.

FIG. 1B depicts a perspective view of a preferred embodiment of thermal eye patch member 20 and frame member 10 of the present invention. Frame member 10 generally comprises support frame and first 11 and second lens 12 member, wherein first 11 and second lens 12 members are attachably connected to support frame. First 11 and second lens 12 members each comprise aperture 13 located at a relatively top end of lens members 11,12, wherein aperture 13 axially aligns with support pin 26 of thermal eye patch member 20 in order to semi-permanently join thermal eye patch member 20 to frame member 10. Thus an outer layer 21 of thermal eye patch 20 adjacently adheres to inner surface 18 of lens 11, 12. As a result, when eye patch member 20 and frame member 10 are connected, a user can easily and efficiently wear eye patch member 20.

Referring back to FIGS. 1A and 1B, in an alternate embodiment, frame member could comprise a single unit, wherein said support frame and said lenses are manufactured as a single device. Additionally, in another alternate embodiment, frame member could comprise said support frame without said lenses, thereby allowing for a means to stack said frame member to a user's existing form of eyewear, as necessary.

Figure 2A:
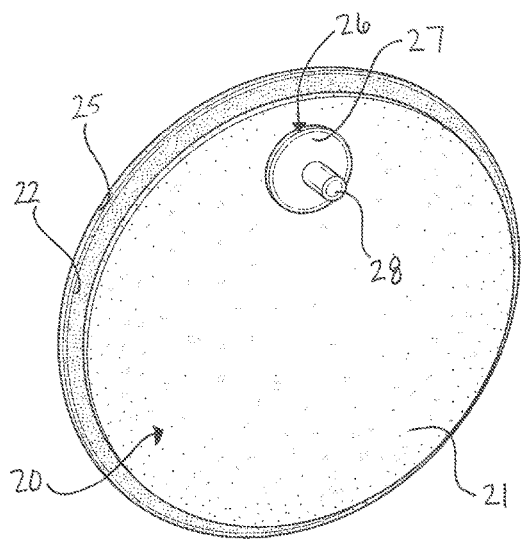
FIG. 2A depicts a perspective view of a preferred embodiment of a thermal eye patch member of the present invention.
Figures 2B, 2C:
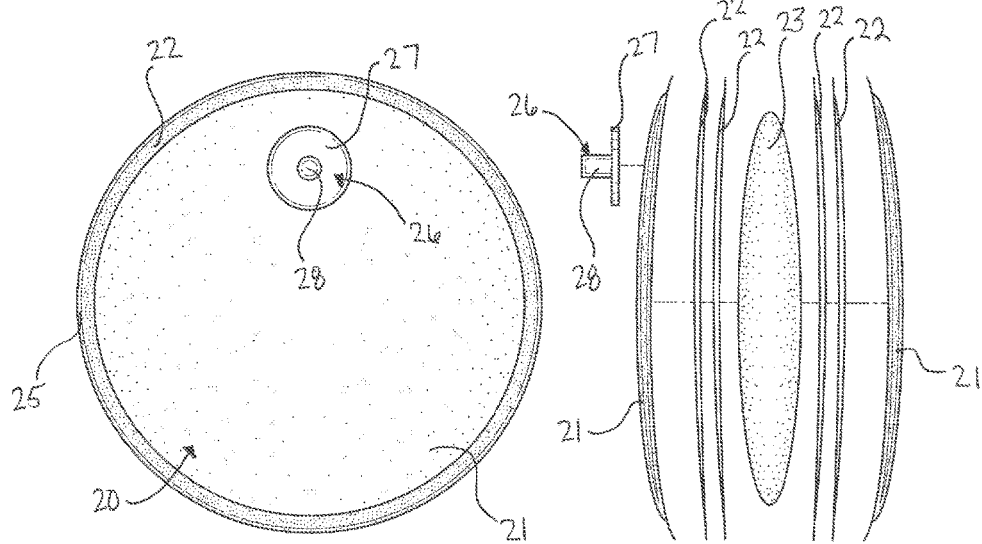
FIG. 2B depicts an end view of a preferred embodiment of a thermal eye patch member of the present invention.
FIG. 2C depicts an exploded side view of a preferred embodiment of a thermal eye patch member of the present invention.

FIG. 2A depicts a perspective view of thermal eye patch member 20 of the present invention, and FIG. 2B depicts an end view of thermal eye patch member 20 of the present invention. Eye patch member 20 comprises a substantially circular configuration that is constructed of a plurality of different layers that are oriented in a relatively stacked configuration, thereby creating a multi-layer thermal pod. By way of illustration, but not limitation, thermal eye patch member 20 comprises a thermal material layer 23, at least one double wall inner bag layer(s) 22, at least one outer covering layer(s) 21, and a heat sealed edge 25.

Heat sealed edge 25 is located around an outer rim of eye patch member 20, thereby bonding all of the layers of eye patch member 20 together when eye patch member 20 reaches a desired temperature. Outer covering layers 21 can be manufactured from a substantially durable, yet soft material, including, but not limited to, a nonwoven synthetic fabric (such as, for example, a bi-component fabric that is made of polyester for strength and polyethylene for softness, currently marketed as Suprel®), or any other similar material exhibiting like characteristics. Further, outer covering layers 21 comprise at least two layers of material, wherein said layers offer protection from bacteria and/or bodily fluid transmission. Inner bag layers 22 can be manufactured from a polyethylene film material, or any other similar material exhibiting like characteristics, in order to act as a barrier and to separate the other layers from one another. Additionally, each inner bag layer 22 comprises at least two layers of material.

Moreover, in a preferred embodiment, thermal material layer 23 comprises a thermal media formula that can be injected into thermal material layer of eye patch member 20. After thermal media is injected, heat sealed edge 25 is closed in order to maintain media and heat within eye patch member 20 of the present invention.

FIG. 2C depicts an exploded side view of thermal eye patch member 20 of the present invention beneficially comprising thermal material layer 23, double wall inner bag layers 22, outer covering layers 21, and heat sealed edge 25. Thermal eye patch member 20 comprises a substantially circular shaped pad-like device having multiple layers that are oriented in a relatively stacked configuration, thereby cooperating to form a temperature retaining eye pad.

In a preferred embodiment, thermal material layer 23 is located in an inner-most layer of eye patch member 20 and comprises a thermal media fluid, or formula, for use in helping to maintain a desire temperature of eye patch member. By way of illustration, but not limitation, thermal media fluid comprises a combination of different substances and materials for use in retaining a specific temperature, either a relatively hot temperature or a relatively cold temperature as necessary (such as, for example, in a similar manner to a relatively gel-like material that is typically used in conventional ice packs), thereby allowing eye patch member to have a relatively higher specific heat capacity, while simultaneously comprising relatively low heat absorption characteristics. Inner bag layers 22 comprise a plastic-like film material in order to separate the thermal material layer and outer covering layers and to act as a barrier in order to prevent any fluid leakage. Outer covering layers 21 comprise a substantially soft, yet durable material and are typically located in an outer-most layer 21 of eye patch member 20, thus encapsulating inner bag layers 22, and ultimately, thermal material layer 23.

Still referring to FIG. 2C, in a preferred embodiment, eye patch member 20 further comprises heat sealed edge 25 and support pin 26, wherein heat sealed edge 25 encircles outer rim of eye patch member 20, and support pin 26 is beneficially located towards a top end of eye patch member 20. Heat sealed edge 25 is beneficially used to bond all of the layers of eye patch member 20 together and to further assist eye patch member 20 in maintaining and regulating a desired temperature. Support pin 26 comprises a substantially circular shaped base member 27 and a relatively outwardly extending rod-like member 28; base member 27 is adjacently positioned along an outer covering layer 21 of eye patch member 20, and rod-like member 28 is used to axially align and be received within aperture 13 of first 11 or second lens 12 of frame member 10 of the present invention.

Figure 3:
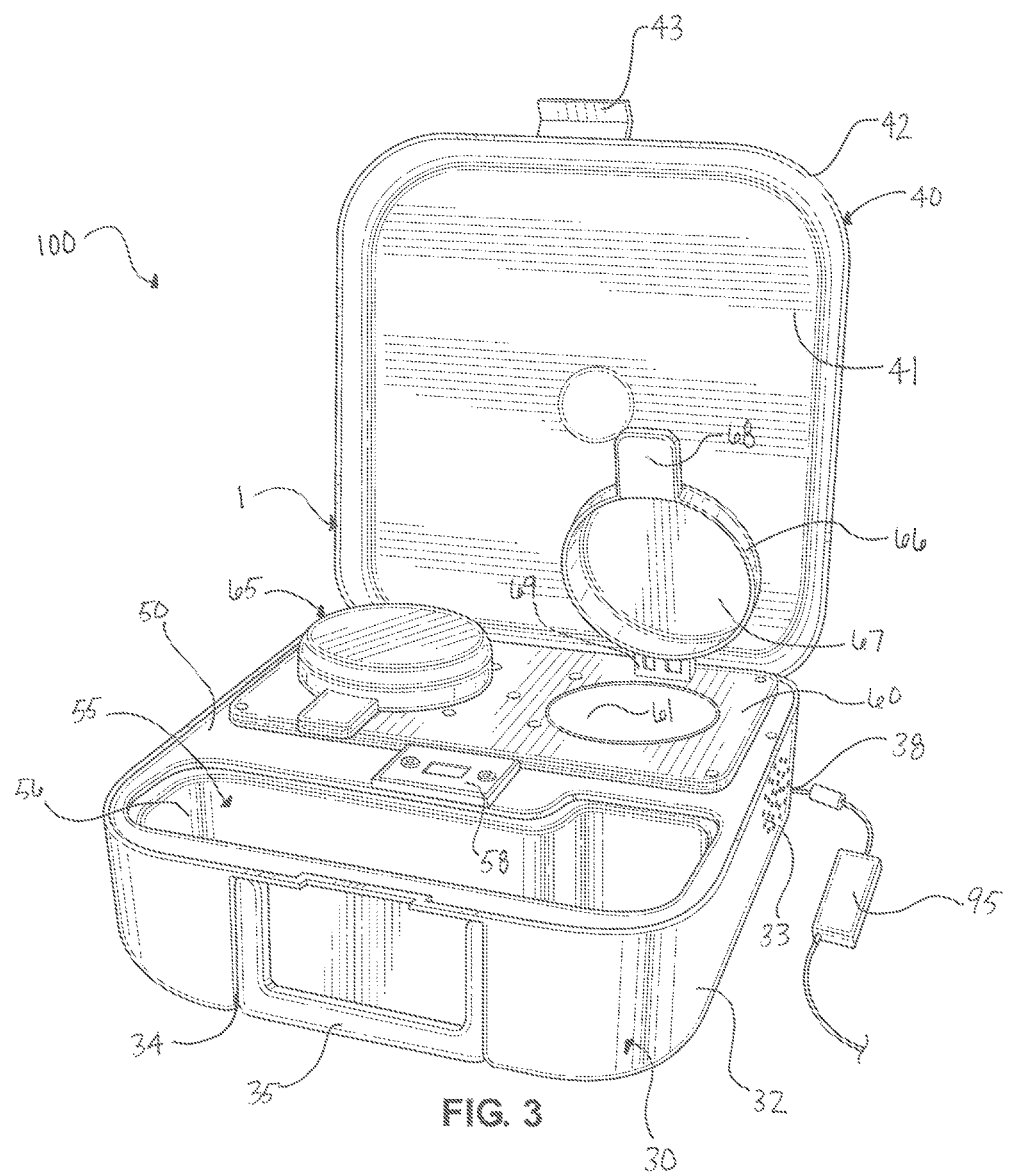
FIG. 3 depicts a perspective view of a preferred embodiment of a thermal eye pod assembly of the present invention in an open configuration.

FIG. 3 depicts a perspective view of thermal eye pod assembly 100 of the present invention with an external shell member 1 in an open configuration. Thermal eye pod assembly 100 generally comprises a container, or external shell member 1, and a plurality of internal components. External shell member 1 can be manufactured from a relatively rigid material, such as, for example, polypropylene, or any other similar material exhibiting like characteristics. External shell member 1 comprises a base member 30, a top member 40, and a handle member 35.

Base member 30 comprises a plurality of substantially planar sides 32 and a substantially planar base 31, and top member 40 comprises a plurality of substantially planar sides 42 and a substantially planar top 41; base member 30 and top member 40 are axially aligned and oriented in a substantially paralleled and mirrored configuration, thereby cooperating to form inner space or chamber 2 for receiving internal components of thermal eye pod assembly 100. Further, base member 30 and top member 40 are attachably connected via a hinge 45, or any other similar means of attachment that allows for external shell member 1 to have a means of opening and closing.

In a preferred embodiment, base member 30 further beneficially comprises a plurality of bores 33 located on said base 31 and/or said sides 32, whereby said bores 33 allow for proper air flow in order to cool a power source that is located within inner chamber 2 of said external shell member 1, and thus, prevent overheating. In addition, base member 30 comprises a plurality of attachment bars 36 located along an inner surface of sides 32 of base member 30. Attachment bars 36 allow for a connection point for an inner top panel 50, or other internal components of the present invention.

In a preferred embodiment, handle member 35 of external shell 1 is located within an inner groove 34 along an outer side of base member 30. Handle 35 comprises a substantially rectangular shape having an inner opening, thus providing a space and a means for a user's hands to reach through said opening and to grip said handle 35. Additionally, external shell member 1 comprises a snap member 43, wherein snap member 43 is located on an outer side of top member 40, thereby allowing top member 40 to beneficially connect and secure to base member 30 in order to close and lock external shell member 1 during transportation of thermal eye pod assembly 100.

Still referring to FIG. 3, thermal eye pod assembly 100 further comprises a plurality of inner components, including, but not limited to, an inner top panel 50, an eye pod support tray 55, a plurality of eye pod cups 65 (a first eye pod cup and a second eye pod cup) and an eye pod support panel 60. Inner top panel 50 can be manufactured from a relatively rigid material, such as, for example, polyvinyl chloride, or any other substantially similar material exhibiting like characteristics. Inner top panel 50 comprises a substantially planar frame having a plurality of sides that are oriented in a relatively squared configuration. Sides of inner top panel 50 coordinate with the dimensions of sides of base member 30 of external shell 1, thereby properly aligning and creating a cohesive fit with base 30 of external shell 1. Additionally, although not depicted in FIG. 3, inner top panel 50 comprises a plurality of apertures having different sizes and configurations for use in allowing the other internal component parts to fit within inner panel 50, and thus, external shell member 1 of the present invention.

Eye pod support tray 55 comprises a substantially rectangular shaped configuration having an inner trough 56, or compartment, for use in holding and storing additional eye pods 20 and frame member 10. Further, eye pod support panel 60 comprises a substantially planar surface with a substantially rectangular configuration, wherein eye pod support panel 60 comprises a plurality of bores 61 (first bore and second bore) that are aligned with eye pod cups 65. In an alternate embodiment, although not illustrated in FIG. 3, eye pod support tray 55 can be manufactured together with inner top panel 50, thereby comprising a single component part.

Eye pod cups 65 comprise a substantially circular configuration and are hingedly attached to eye pod support panel 60. When eye pod cups 65 are in an open configuration, first bore 61 and second bore 61 are visible; when eye pod cups 65 are in a closed configuration, bores 61 are typically not visible. Moreover, eye pod cups 65 comprise a housing 66, or holding compartment, for use in having a layer of insulation located along an underside 67 of eye pod cup, while still being able to store thermal eye patch members 20. Eye pod cups 65 further comprise a tab member 68, wherein said tab member 68 outwardly extends from eye pod holding compartment 66. Tab member 68 allows a user to easily lift and lower eye pod cups 65 of the present invention in order to open or close eye pod cups 65 as necessary.

Additionally, although not illustrated in FIG. 3, eye pod support panel 60 aligns with and is adjacently positioned on top of a transfer plate. Thus, when in a closed position, eye pod cups 65 directly contact a surface of transfer plate, thereby allowing for a means of heat transfer relative to ambient conditions. Further, eye pod support panel 60 maintains a means of attachably connecting to eye pod cups 65 via a hinged connection 69, or any other similar attachment means.

Figure 4:
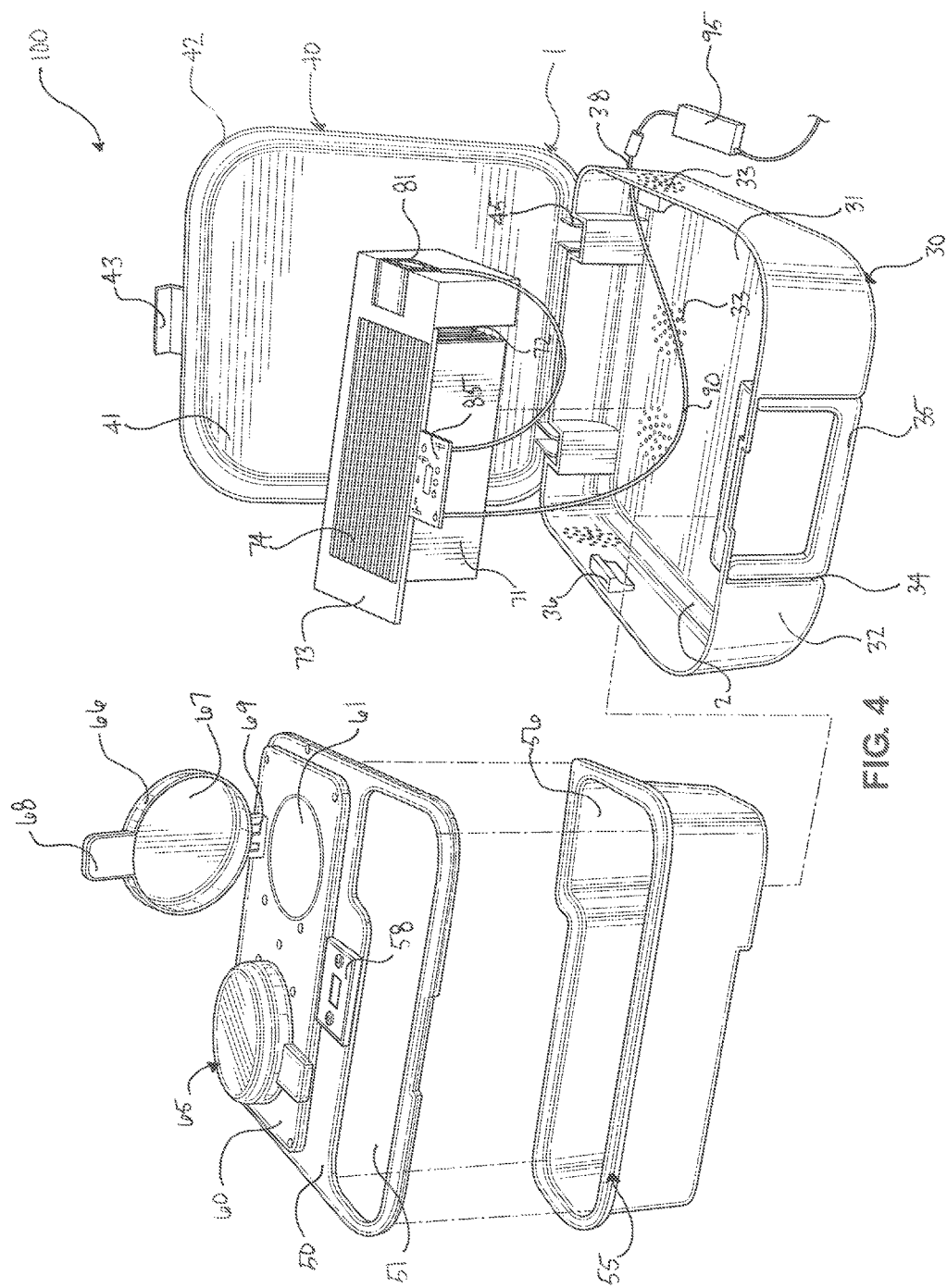
FIG. 4 depicts an exploded perspective view of a preferred embodiment of a thermal eye pod assembly of the present invention.

FIG. 4 depicts an exploded view of said thermal eye pod assembly 100 of the present invention generally comprising external shell member 1 and an electrical control system, including, but not limited to, a power source 95, a heating/cooling source 73, a circuit board 85, a fan 81, and a variety of different types of insulation. Base member 30 and top member 40 of external shell 1 are axially aligned and oriented in a substantially paralleled configuration, thereby cooperating to form inner space or chamber 2 for receiving internal components, such as, for example, electric control system of thermal eye pod assembly 100. Further, base member 30 and top member 40 are attachably connected via a hinge 45, or any other similar means of attachment that allows for external shell member 1 to have a means of opening and closing.

Electrical control system comprises a substantially rigid structure that is capable of supporting a plurality of different components and can be pre-assembled, pre-wired, pre-programmed, and integrated onto a panel that can be mounted within an inner chamber 2 of external shell member 1 of thermal eye pod assembly 100. Further, electrical control system comprises a number of electrical components that automate control and functionality of ancillary devices, including, but not limited to, a fan(s), a power supply, heat pump(s), receptacle(s), and a plurality of switches.

Additionally, electrical control system comprises, by way of illustration, but not limitation, power source 95 that monitors and controls power usage within thermal eye pod assembly; a Peltier heat pump 73 that transfers and regulates temperature; control board switch package 85 that supplies power to a fan 81 when said circuit is activated; and, fan 81 that is used to push ambient air from outside of heat pump 73 over a plurality of heat exchanger/cooling fins 74 within thermal eye pod assembly 100. Cooling fins 74 comprise a plurality of projections that are equidistantly spaced apart in order to allow excess heat and ambient air away from the device, as necessary. In addition, it is to be observed that specific configurations and component parts to electrical control system can vary depending on a variety of different factors.

Further, by way of illustration, but not limitation, Peltier heat pump 73 is beneficially used in thermal eye pod assembly 100 of the present invention because of said heat pump's 73 ability to transfer heat from one side of the device to the other, while being able to regulate a desired temperature for use in either heating and/or cooling.

Still referring to FIG. 4, thermal eye pod assembly 100 generally comprises a transfer block 71, a transfer plate, and multiple means of insulation. Transfer block 71, or heat transfer mechanism, and transfer plate can be manufactured from a relatively rigid material, such as, for example, aluminum, or any other material exhibiting like characteristics. Although not illustrated in FIG. 4, transfer plate comprises a substantially planar surface and is positioned on top of transfer block 71, and further surrounded and protected by a layer of insulation. Insulation can typically be manufactured from a plastic material, such as, for example, polystyrene, or any other similar material exhibiting desired characteristics.

Additionally, although not depicted in FIG. 4, transfer plate comprises a relatively thin layer of insulation bonded to an underside of said transfer plate and a thermal switch device attachably connected to the underside of transfer plate. Thermal switch device is a regulator that is designed to trip a circuit into an "off" position when a level of heat on transfer plate reaches approximately one hundred and forty (140) degrees Fahrenheit, or sixty (60) degrees Celsius. As the temperature on transfer plate decreases, thermal switch closes, thereby allowing device to continue heating transfer plate. As a result, heat can be maintained at a relatively safe temperature for thermal eye pod assembly 100.

In a preferred embodiment, thermal eye pod assembly 100 comprises power supply 95 with a power cord that is beneficially powered by an AC/DC converter. Base member 30 of external shell member 1 comprises power receptacle 38, or aperture, for use in providing a connection point for power supply 95 to connect to external shell 1 of the present invention. Power receptacle 38 is located on a side of base member 30 opposite of handle 35 and is positioned towards a relatively bottom end of said side 32.

As depicted in FIG. 4, it is to be observed that electrical control system comprising heat pump 73 with heat exchange projections 74, fan 81, and control board switch 85, is shown in an inverted position for illustrative purposes. In a preferred embodiment, although not illustrated in FIG. 4, electrical control system would be rotated in a relatively 180 degree position prior to placement within inner chamber 2 of external shell 1 of the present invention.

Still referring to FIG. 4, in a preferred embodiment, inner top panel 50 coordinates with the dimensions of sides of base member 30 of external shell 1, thereby properly aligning and creating a cohesive fit within base 30 of external shell 1. Additionally, inner top panel 50 comprises a plurality of apertures having different sizes and configurations for use in allowing the other internal component parts to fit within inner panel 50, and thus, external shell member 1 of the present invention.

As illustrated in FIG. 4, eye pod support tray 55 comprises a substantially rectangular shaped configuration having an inner trough 56, or compartment, for use in holding and storing additional eye pods 20 and frame member 10. Further, eye pod support panel 60 comprises a substantially planar surface with a substantially rectangular configuration, wherein eye pod support panel 60 comprises a plurality of bores 61 that are aligned with eye pod cups 65. Eye pod support panel 60 aligns with and is adjacently positioned on top of a transfer plate. Thus, when in a closed position, eye pod cups 65 directly contact a surface of transfer plate, thereby allowing for a means of heat transfer to eye pods 20 being housed within eye pod cups 65.

In a preferred embodiment, still referring to FIG. 4, eye pod cups 65 comprise a housing compartment 66 for use in having a layer of insulation located along an underside 67 of eye pod cup 65 and still being able to store thermal eye patch members 20. Eye pod cups 65 further comprise a tab member 68, wherein said tab member 68 outwardly extends from eye pod holding compartment 66. Tab member 68 allows a user to easily lift and lower eye pod cups 65 of the present invention.

As a result, when in operation, at least one thermal eye patch member 20 can be placed within housing compartment 66 of eye pod cup 65. Eye patch member 20 will be in direct contract with transfer plate via bore 61 of eye pod support panel 60. Once a desired temperature is achieved via heat pump, and then transferred to transfer plate, said desired temperature will either heat or cool thermal eye patch member 20, as necessary. The temperature of transfer plate, and thus, thermal eye patch member 20 will be maintained through the various means of insulation within inner chamber 2 of external shell 1 of the present invention. When eye patch members 20 have achieved a desired temperature, a user will open tab 68 of eye pod cup 65, remove eye patch member 20, and then align eye patch 20 with lens 11, 12 of frame member 10. Eye patch 20 can then be secured to frame member 10 via support pin 26 of eye patch 20 being received within aperture 13 of lens 11, 12, thereby giving a user freedom and ability to wear eye patch 20 in a hands-free manner.

The above-described invention has a number of particular features that should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:

1. An apparatus adapted for therapeutic thermal treatment of orbital regions comprising:
    a frame adapted to be worn over a portion of a face;
    at least one lens disposed within said frame,
    at least one pod member adapted to be secured against or in proximity to an orbital region; and
    wherein said at least one pod member is removably attached to said at least one lens.

2. The therapeutic thermal treatment apparatus of claim 1, wherein said pod member further comprises a bag containing a thermal media fluid.

3. The therapeutic thermal treatment apparatus of claim 1, wherein said pod member further comprises at least one covering disposed over said bag.

4. The therapeutic thermal treatment apparatus of claim 3, wherein said thermal media fluid has a sufficient specific heat capacity to retain heat when said thermal media fluid is heated above an ambient temperature.

5. The therapeutic thermal treatment apparatus of claim 3, wherein said thermal media fluid has a sufficient heat absorption capacity to resist absorption of ambient heat when said thermal media fluid is chilled below an ambient temperature.

6. The therapeutic thermal treatment apparatus of claim 1, further comprising a support pin extending from said pod member, and an aperture disposed on said frame for receiving said support pin.

7. The therapeutic thermal treatment apparatus of claim 1, further comprising a portable assembly for selectively heating or cooling said at least one pod member.

8. A method for thermally treating an orbital region comprising:
    selectively heating or cooling at least one pod member relative to an ambient temperature,
    providing a frame having at least one lens,
    affixing the at least one pod member to the at least one lens,
    placing the frame, lens and pod member on the face,
    wearing said frame member with the pod member against a face, and
    positioning said pod member against or in proximity to an orbital region.

9. The method of claim 8, further comprising providing an assembly for selectively heating or cooling said at least one pod member.

10. The method of claim 8, wherein providing the at least one pod member further comprises providing at least one bag and providing a thermal media fluid in the bag.

11. The method of claim 10, wherein providing the pod member further comprises providing at least one covering and disposing the covering over the bag.

12. The method of claim 10, wherein said thermal media fluid has a sufficient specific heat capacity to retain heat when said thermal media fluid is heated above an ambient temperature.

13. The method of claim 10, wherein said thermal media fluid has a sufficient heat absorption resistance capacity to resist absorption of ambient heat when said thermal media fluid is chilled below an ambient temperature.

14. The method of claim 8, wherein the providing the assembly for selectively heating or cooling the at least one pod member further comprises:
    providing a shell having a base defining an inner chamber,
    providing a receptacle disposed within said inner chamber, the receptacle being adapted to receive said pod member, and
    providing a cooling assembly disposed in said inner chamber, the cooling assembly being adapted to selectively cool said at least one pod member when the pod member is disposed in the receptacle.

15. The method of claim 14, wherein the providing the assembly for selectively heating or cooling said at least one pod member further comprises providing a heating assembly adapted to selectively heat said at least one pod member when the pod member is disposed in said receptacle.

16. The method of claim 14, wherein the providing an assembly for selectively heating or cooling said at least one pod member further comprises providing an electrical heater or electrical cooling device.

17. The method of claim 8, further comprising providing a support pin extending from said pod member, and providing an aperture disposed on the at least one lens adapted for receiving the support pin.

* * * * *